United States Patent [19]
Donohue

[11] 3,985,137
[45] Oct. 12, 1976

[54] TIP FOR VETERINARY SURGICAL CAUTERIZATION INSTRUMENT

[76] Inventor: Brian T. Donohue, W. Milford Animal Hospital, Oakridge Road (Rte. 23), Oakridge, N.J. 07438

[22] Filed: Sept. 27, 1974

[21] Appl. No.: 510,109

[52] U.S. Cl. .................................. 128/303.17
[51] Int. Cl.² .............................. A61B 17/36
[58] Field of Search ...... 30/140; 128/303.1, 303.13, 128/303.17; 219/233, 235

[56] References Cited
UNITED STATES PATENTS

| | | | |
|---|---|---|---|
| 958,753 | 5/1910 | Meyer | 219/233 X |
| 2,050,904 | 8/1936 | Trice | 219/235 X |
| 2,102,270 | 12/1937 | Hyams | 128/303.17 |
| 2,734,986 | 2/1956 | Gameros | 219/235 X |
| 2,955,188 | 10/1960 | Campo | 219/235 X |
| 3,532,095 | 10/1970 | Miller | 128/303.13 |
| 3,645,265 | 2/1972 | Majzlin | 128/303.13 |

*Primary Examiner*—Channing L. Pace
*Attorney, Agent, or Firm*—James J. Cannon, Jr.; James J. Cannon

[57] ABSTRACT

A tip for a veterinary surgical cauterization instrument is disclosed in which an electric current conducting heat generating tip has a non-conducting heat resistant sheath surrounding a portion of the tip a selected distance from the tip apex.

1 Claim, 4 Drawing Figures

TIP FOR VETERINARY SURGICAL CAUTERIZATION INSTRUMENT

BACKGROUND OF THE INVENTION

1. Field of the Invention

The invention resides in the field of veterinary surgical devices and more particularly to a specialized tip for a cauterization instrument.

2. Description of the Prior Art

The anal sacs of the dog are homologous to the scent glands of the skunk. They are expressed in defense or when the dog is aggravated — thus apparently under control of the sympathetic nerves of the autonomic nervous system. The anal sacs are present in all dogs; however, they are functional in only a small percentage. These dogs with functional anal sacs are susceptable to anal sac infections and associated complications.

The anal sacs, one on each side of the anal canal, are approximately spherical sacs which are located between the inner smooth and the outer striated sphincter muscle of the anus. The anal sacs vary in size from a pea to a marble, the average diameter being a little less than one centimeter. The excretory duct of each sac is about 5 mm. long and 2 mm. in diameter, and opens near the cranial end of the furrow between the dorsal and lateral parts of the inner cutaneous zone of the anus adjacent to the intermediate zone. In about 10% of the dogs the opening of the anal sac is located in the broad depression formed by the lateral arch of the anocutaneous line on each side. They frequently become enlarged, owing to accumulated secretion, or they may become abcessed and painful. Infrequently they rupture to the outside, lateral to the anus, producing anal fistulas.

This invention pertains to an instrument for cauterization of these anal sacs. The inventor knows of no device in the prior art or medical literature which will function in the manner described herein. Some devices designed to operate as diathermy instruments use protective sheaths of one form or another but the metallic elements of diathermy units are not complete conductors using instead the tissue to complete the current path. Thus they are structurally different and operate in a different way from the cauterization device which is the subject of the present invention.

SUMMARY OF THE INVENTION

The invention particularly pertains to a modified cautery tip for cauterizing the anal sacs of a dog without destroying the orifices of the sacs.

A dog has two nearly useless anal sacs in the area of its anus. A small orifice from each anal sac leads to the anal area. The anal sacs secrete a semi-liquid substance which passes out through the orifices. When the orifices clog, the anal sacs swell and cause great pain during defecation. The present medical procedure for correcting this problem is surgical removal of the anal sacs.

The invention disclosed herein is similar to a standard tip for a cautery instrument or gun modified by the addition of a heat resistant, non-porous ceramic material sheath. In use, the tip is inserted through the orifice to the anal sac, the exposed part of the tip being in the anal sac and the ceramic sheathed part in the orifice. Heat is applied. The anal sac is cauterized, the orifice is unaffected and the tip is removed.

The non-porous ceramic portion of this instrument is highly resistant to heat which enables the rest of the instrument to heat to extremely high temperatures for cauterization procedures. This particular operation can be carried out in four seconds, as opposed to the surgical practice which requires 1 ½ hours.

The cautery gun into which the tip is inserted is attached by an electrical wire to a box functioning to regulate the amount of current and thus the amount of heat passing into the tip. The tip apex is usually comprised of tungsten supported by two stainless steel arms. The design of the tungsten tip varies with the nature of the operation being performed. Pressing a control button on the gun heats the instrument rapidly. It is inserted into the orifice near the dog's anus, destroying the sac itself with heat, and removed. In aforementioned surgical operation, the dog often defecated on the incision line, prior to healing, leading to bacterial complications.

These and other features are more clearly shown in the drawings and the description of the preferred embodiment which follow.

DESCRIPTION OF THE PREFERRED EMBODIMENT

Figure 1:
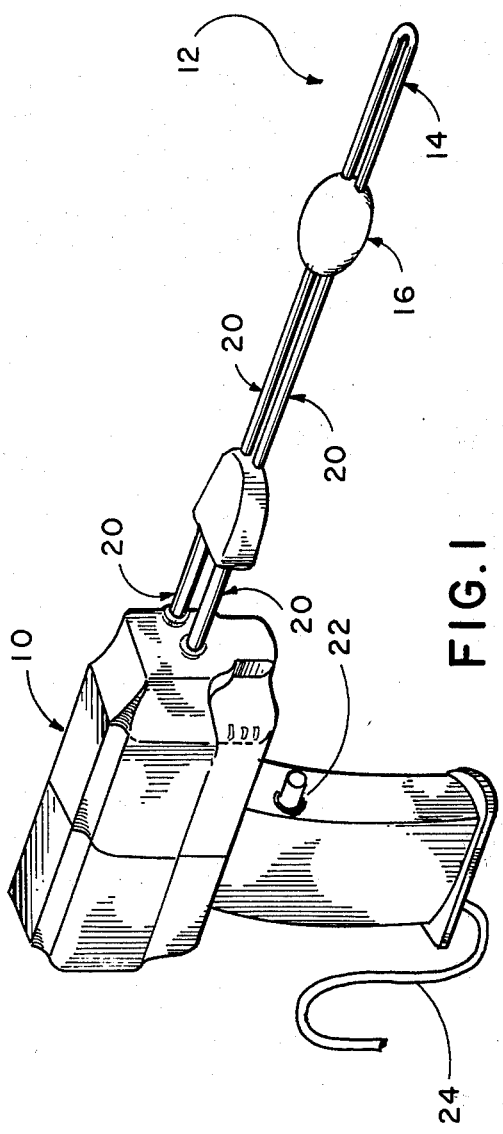
FIG. 1 is a diagrammatic view of a cauterization instrument employing the tip of the invention.

Referring to FIG. 1, there is shown a view of the invention inserted in a cautery instrument on gun 10. The tip 12 is comprised of a heat generating elongated U-shaped electrical conductor 14 and a heat resistant sheath 16. The tip is preferably comprised of a high electrical resistance metal such as tungsten and the sheath of a non-porous ceramic. An additional sheath 18 comprised of plastic may be used to adapt the tip 12 to a specific gun. Rods 20 optionally comprised of brass coated with stainless steel for strength, provide the contact with the gun and support the tip. The rods and the tip are connected within the sheath 16.

A trigger or button 22 is used to activate the unit which is connected by cord 24 to a heat control box 26 with dial 28 for adjusting the maximum flow of current which in turn regulates the heat output of the tip. The control box is connected to a power source by cord 30. The unit is a standard unit and in and of itself forms no part of the invention. The use of the device is as described in the summary above.

Figure 2:
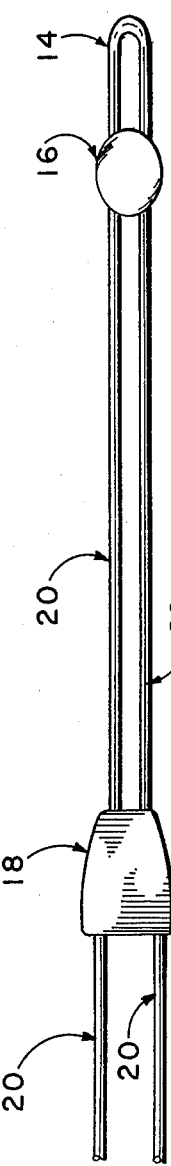
FIG. 2 is a plan view of a tip showing one shape of heat resistant sheath.
Figure 3:
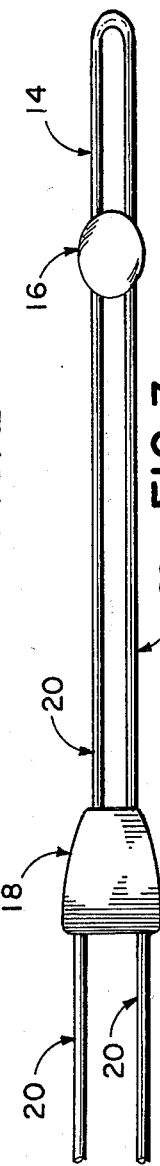
FIG. 3 is a plan view of a tip showing an alternative by placed heat resistant sheath.
Figure 4:
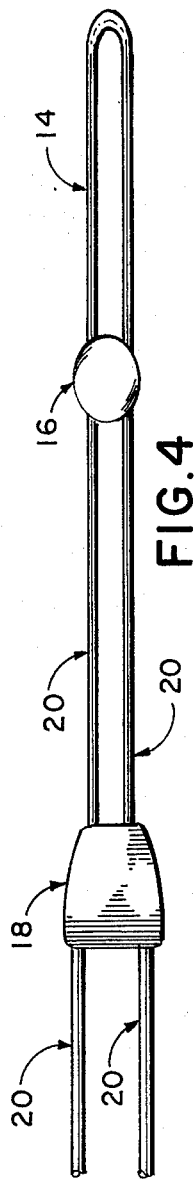
FIG. 4 is a plan view of a tip showing yet another placement of the heat resistant sheath.

Referring to FIGS. 2, 3, and 4, there are shown plan views of the tip disclosing a variety of possible placements of sheath 16 and a variety of lengths for tip 14 which may be employed in the invention and which are adapted to various size dogs.

Within limits, this variety of placements may be obtained by providing channels within sheath 16 to snugly slide forward or rearward along tungsten tip 14 while not exposing any tungsten along the rearward side of sheath 16.

The cauterization procedure for use of the cauterization instrument employing the tip of this invention is as follows. First the anal sacs are expressed. Then the heating tip element with the unit to supply heat to the tip element is inserted into the anal sac through the orifice until the protective heat shield is pressed against the orifice. With the pressure of the heating tip element into the anal sac, the end result is that the sac is now formed in a straight line with its sides in close proximity to the heating element.

The unit is then turned on for three seconds, during which time the secretory tissue is seared and adhered to the heating element. Within this time the secretory tissue of the anal sac is partially, if not entirely, destroyed to a depth of one millimeter. The heating tip element is then twisted 180° in order to obtain better contact with more anal sac tissue and once again the heating element is turned on for three seconds.

The advantages of this procedure using the tip of the present invention are that there is no surgical incision line or other surgical preparation; there are no infections due to cauterization as opposed to open surgery; the procedure takes only five to fifteen seconds; and the procedure and the tip of the invention are very inexpensive.

Having disclosed the above, certain modifications in shape and material may become obvious to those skilled in the art. Accordingly the scope of the invention is defined by the following claims.

What is claimed is:

1. In an electrosurgical cauterization instrument, for insertion into a body cavity, having a variable current control from a power source, an insulated handle having an electrode receiving end and an operative electrode tip comprised of a suitable electrical resistance material capable of producing heat, wherein the improvement comprises:

a slidable ovular protective insulating sheath, being positioned near said tip, for insertion into an orifice of said body cavity resulting in spreading and protection of healthy and sensitive tissue during a cauterization procedure, said slidable sheath having two longitudinal bores through which a U-shaped electrode forming said tip passes.

* * * * *